United States Patent
Amatulli et al.

(10) Patent No.: US 8,552,157 B2
(45) Date of Patent: Oct. 8, 2013

(54) C-KIT ANTIBODIES AND USES THEREOF

(75) Inventors: Michael Amatulli, Brooklyn, NY (US); Laura Ann Breen (nee Brennan), Sunnyside, NY (US); Keren Paz, Tenafly, NJ (US)

(73) Assignee: ImClone LLC, Indianapolis, IN (US)

( * ) Notice: Subject to any disclaimer, the term of this patent is extended or adjusted under 35 U.S.C. 154(b) by 46 days.

(21) Appl. No.: 13/462,853

(22) Filed: May 3, 2012

(65) Prior Publication Data

US 2012/0288506 A1 Nov. 15, 2012

Related U.S. Application Data

(60) Provisional application No. 61/485,255, filed on May 12, 2011.

(51) Int. Cl.
*C07K 16/28* (2006.01)
*C07K 16/00* (2006.01)
*A61K 39/395* (2006.01)

(52) U.S. Cl.
USPC .............. 530/388.24; 530/388.1; 530/387.1; 424/145.1; 424/130.1

(58) Field of Classification Search
None
See application file for complete search history.

(56) References Cited

U.S. PATENT DOCUMENTS

2007/0253951 A1* 11/2007 Ng et al. ............... 424/133.1

FOREIGN PATENT DOCUMENTS

| WO | WO 2007/127317 A2 | 11/2007 |
| WO | WO 2008/153926 A2 | 12/2008 |
| WO | WO 2010/053814 A1 | 5/2010 |

OTHER PUBLICATIONS

Garrido et al. J. Invest Dermatol 2010, 130:20-27.*
Wang et al. PNAS 2005, 102:1104-1109.*
Micke et al. Clinical Cancer Research 2003, 9:188-194.*
Uccini et al., "Clinical and Molecular Evidence for c-kit Receptor as a Therapeutic Target in Neuroblastic Tumors," Clinical Cancer Research 11:380-389 (2005).
Vitali, et al., "c-Kit is Preferentially Expressed in Mycn-Amplified Neuroblastoma and its Effect on Cell Proliferation is Inhibited In Vitro by STI-571," Int. J. Cancer 106:147-152 (2003).
Cohen, P., et al., "Expression of stem cell factor and c-kit in human neuroblastoma," BLOOD, 84(10):3465-3472 (1994).
Kurosawa, K., et al., "Immobilized anti-KIT monoclonal antibody induces ligand-independent dimerization and activation of Steel factor receptor: biologic similarity with membrane-bound form of Steel factor rather than its soluble form," BLOOD, American Society of Hematology, US, 87(6): 2235-2243 (Mar. 1996).
Lennartsson, J., et al., "The stem cell factor receptor/c-Kit as a drug target in cancer," Current Cancer Drug Targets, 6:561-571 (Jan. 2006).
Document from WIPO Examination of related application: "Written Opinion of the International Search Authority," Date of completion of this opinion as per Form PCT/ISA/210: Date of the actual completion of the International search: Jul. 18, 2012, Date of mailing of the International search report: Aug. 2, 2012.
Document from WIPO Examination of related application: "International Search Report," Form PCT/ISA/210, Date of the actual completion of the International search: Jul. 18, 2012, Date of mailing of the International search report: Aug. 2, 2012.

* cited by examiner

*Primary Examiner* — Sharon Wen
(74) *Attorney, Agent, or Firm* — Danica Hostettler

(57) ABSTRACT

This invention is directed to antibodies that specifically bind to an extracellular domain of human c-Kit, pharmaceutical compositions comprising these antibodies, and their use in treating cancer.

8 Claims, 2 Drawing Sheets

US 8,552,157 B2

C-KIT ANTIBODIES AND USES THEREOF

This application claims the priority of U.S. Provisional Application No. 61/485,255 filed May 12, 2011.

This invention is directed to antibodies that specifically bind to an extracellular domain of human c-Kit, pharmaceutical compositions comprising these antibodies, and their use in treating diseases or disorders associated with expression and/or activity of c-Kit such as a tumor, a cancer, and/or a cell proliferative disorder.

c-Kit is a receptor tyrosine kinase also known, for example, as stem cell factor (SCF) receptor or CD-117. c-Kit and its ligand, SCF, mediate various biological functions including hematopoiesis, melanogenesis, erythropoiesis, spermatogenesis, carcinogenesis, fibrosis, inflammation, mast cell differentiation and proliferation, and immunologic processes.

GLEEVEC® (imatinib mesylate) and SUTENT® (sunitinib malate) are approved and marketed pharmaceutical small molecule products that inhibit multiple receptor tyrosine kinases including c-Kit. However, it is now clear that such therapies, generally provide limited benefit in their approved indications because tumor cells often have or rapidly develop mutationally mediated drug resistance.

Antibodies to human c-Kit have been reported previously. However, known c-Kit antibodies are less than desirable for use in treating cancer because they inhibit c-Kit internalization, stimulate c-Kit agonist activities, e.g., c-Kit phosphorylation, in tumor cells, or lack other attributes that are optimal for their effective use as therapeutic anti-cancer agents. For example, WO 2007/127317 discloses humanized c-Kit antibodies and data relevant thereto relating primarily to the effect of the antibodies on mast cells, hematopoiesis, melanogenesis, and spermatogenesis. Notably, the antibodies described in WO 2007/127317 were reported to "potently inhibit SCF-mediated c-Kit phosphorylation and internalization in MO7e cells."

Accordingly, the present invention provides alternative monoclonal antibodies that specifically target the extracellular domain (ECD) of human c-Kit. The invention also provides monoclonal antibodies that specifically target the ECD of human c-Kit that are capable of inducing internalization and/or degradation of plasma membrane bound c-Kit without inducing c-Kit agonist activities, e.g., c-Kit phosphorylation, in tumor cells, and/or have other clinical attributes (e.g., improved solubility, in vitro or in vivo stability, or other pharmacokinetic properties) that are advantageous for their effective use as therapeutic anti-cancer agents. Such antibodies are expected to be more effective in treating cancer, and advantageously, delay or prevent acquisition of mutation mediated drug resistance and/or treat cancers which are resistant to known therapies. Therefore, the c-Kit antibodies described herein meet a critical need in the art. One aspect of this invention pertains to an antibody that specifically binds to an extracellular domain of human c-Kit consisting of the amino acid sequence as in SEQ ID NO: 20, the antibody comprising a heavy chain variable region (HCVR) and a light chain variable region (LCVR), wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6).

Another aspect of this invention pertains to a pharmaceutical composition comprising an antibody that specifically binds to an extracellular domain of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6), together with at least one pharmaceutically acceptable carrier, diluent or excipient.

In one aspect, the invention provides an antibody that specifically binds to an extracellular domain of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6) for use in therapy.

Another aspect of this invention provides an antibody that specifically binds to an extracellular domain of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6) for use in treating cancer.

Another aspect of this invention provides the use of an antibody that specifically binds to an extracellular domain of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6), for the manufacture of a medicament for treating cancer, a tumor, and/or a cell proliferative disorder.

Another aspect of this invention provides a method of treating cancer in a human in need thereof, comprising administering to said human a therapeutically effective amount of an antibody that specifically binds to an extracellular domain of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6).

In one aspect, the invention provides methods of treating cancer in a human in need thereof, comprising administering to said human a therapeutically effective amount of effective amount of an antibody that specifically binds to an extracellular domain of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6), in combination with a therapeutically effective amount of at least one other therapeutic agent. In a preferred embodiment the other therapeutic agent is an anti-cancer agent.

Another aspect of this invention provides isolated nucleic acid molecules encoding the c-Kit antibodies of the invention, expression vectors comprising the nucleic acid molecules, and host cells comprising the nucleic acid molecules.

DETAILED DESCRIPTION OF THE INVENTION

Figure 1:
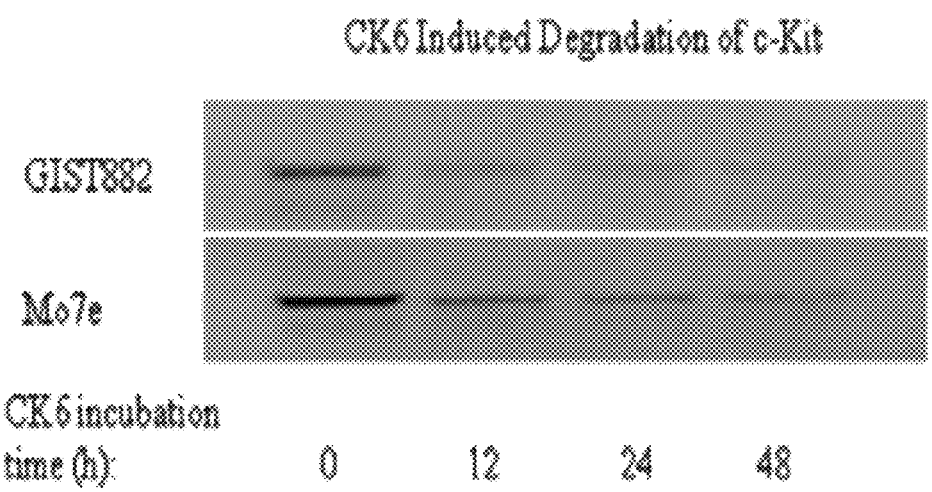
FIG. 1 depicts a western blot of total c-Kit detected in total cell lysates of human tumor cell lines, Mo7e and GIST882, before and after treatment of the cells in vitro with anti-c-Kit mAb, CK6. Anti-c-Kit mAb CK6 dramatically induced degradation of c-Kit expressed by human tumor cells in a time-dependent manner.
Figure 2:
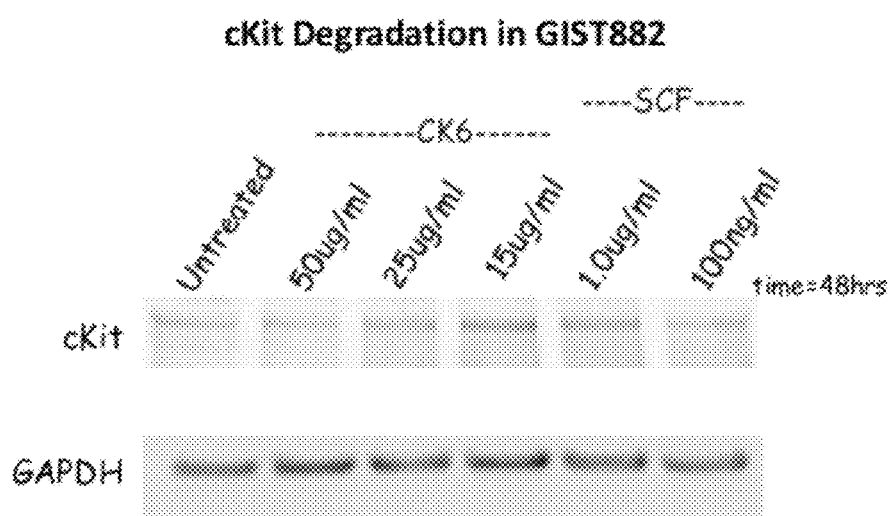
FIG. 2 depicts a western blot of total c-Kit detected in total cell lysates of a human tumor cell line, GIST882, with and without anti-c-Kit mAb, CK6. Anti-c-Kit mAb CK6 is not observed as significantly inducing degradation of c-Kit expressed by GIST882 human tumor cells in a time-dependent manner.
Figure 3:
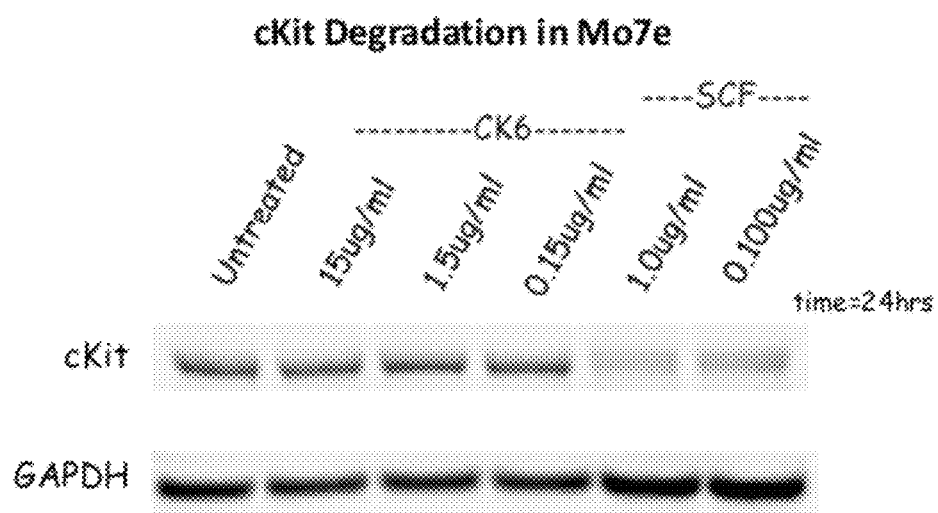
FIG. 3 depicts a western blot of total c-Kit detected in total cell lysates of a human tumor cell line, Mo7e, with and without anti-c-Kit mAb, CK6. Anti-c-Kit mAb CK6 is not observed as significantly inducing degradation of c-Kit expressed by Mo7e human tumor cells in a time-dependent manner.
Figure 4:
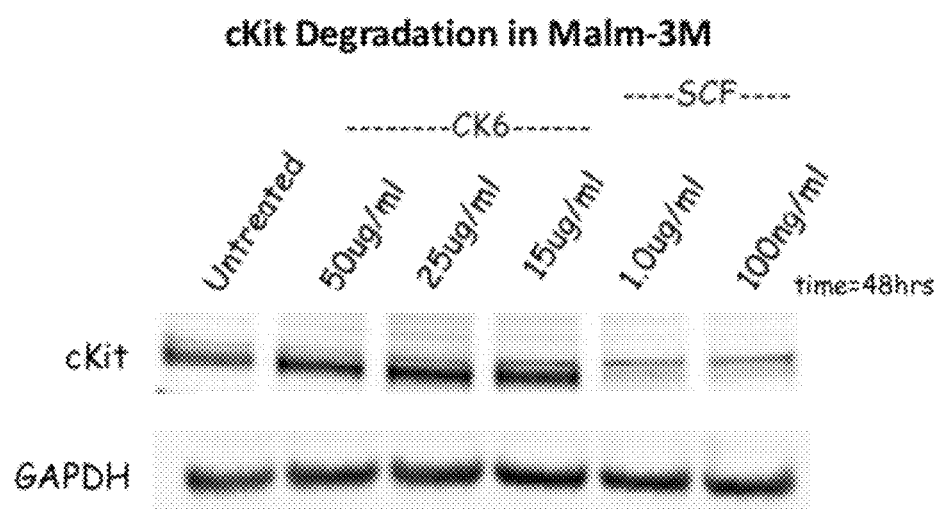
FIG. 4 depicts a western blot of total c-Kit detected in total cell lysates of a human tumor cell line, Malm-3M, with and without anti-c-Kit mAb, CK6. Anti-c-Kit mAb CK6 is not observed as significantly inducing degradation of c-Kit expressed by Malm-3M human tumor cells in a time-dependent manner.

The present invention provides antibodies that specifically bind the ECD of human c-Kit that are useful for, e.g., treatment of diseases or disorders associated with expression and/or activity of c-Kit such as a tumor, a cancer, and/or a cell proliferative disorder.

The term "antibody" as used herein refers to a monoclonal antibody, unless otherwise indicated. "Monoclonal antibody" and its abbreviation "mAb" is intended to refer to an antibody that is derived from a single copy or clone, including e.g., any eukaryotic, prokaryotic, or phage clone, and not the method by which it is produced. An antibody, as the term is used herein, can be an intact antibody (comprising a complete or full length Fc region) or a portion or fragment thereof comprising an antigen-binding portion, e.g., a Fab fragment, Fab' fragment, or F(ab')2 fragment, that binds to the ECD of human c-Kit consisting of the amino acid sequence as in SEQ ID NO: 20. For example, antibody fragments capable of binding to the ECD of c-Kit and which are embraced by the present invention include, but are not limited to, bivalent fragments such as (Fab')$_2$ with inter-chain disulfide bonds intact, monovalent fragments such as Fab (Fragment, antigen binding) which refers to the fragments of the antibody consisting of LCVR-CL and HCVR-CH1 domains and do not retain the heavy chain hinge region (e.g., by papain digestion), Fabs which retain the heavy chain hinge region, Facb (e.g., by plasmin digestion), F(ab')$_2$, Fab' which lack disulfide bonds, pFc' (e.g., by pepsin or plasmin digestion), Fd (e.g., by pepsin digestion, partial reduction and re-aggregation) and Fv or scFv (e.g., by molecular biology techniques; see, Pluckthun, *The Pharmacology of Monoclonal Antibodies*, vol. 113, Rosenburg and Moore eds., Springer-Verlag, New York, pp 269-315, 1994). Antibody fragments are also intended to include, e.g., domain deleted antibodies, linear antibodies, single chain antibodies, single domain antibodies, multivalent single chain antibodies, multi-specific antibodies formed from antibody fragments including diabodies, triabodies, and the like that specifically bind the ECD of human c-Kit consisting of the amino acid sequence as in SEQ ID NO: 20. It is understood that regardless of whether antigen-binding fragments or portions are specified, the term "antibody" as used herein includes such fragments or portions as well as single chain forms, unless indicated otherwise.

The light chain can comprise one variable domain (abbreviated herein as LCVR) and/or one constant domain (abbreviated herein as CL). The light chains of human antibodies (immunoglobulins) are either kappa (κ) light chains or lambda (λ) light chains. The expression LCVR, as used herein, is intended to include both the variable regions from kappa-type light chains (Vκ) or from lambda-type light chains (Vλ). The heavy chain can also comprise one variable domain (abbreviated herein as HCVR) and/or, depending on the class or isotype of antibody, three or four constant domains (CH1, CH2, CH3 and CH4; abbreviated herein collectively as CH). Human IgG1 is the preferred isotype for the antibodies of the present invention.

Three regions, called hypervariable or complementarity-determining regions (CDRs), are found in each of LCVR and HCVR, which are supported by less variable regions called frameworks (abbreviated herein as FR). Amino acids are assigned to a particular CDR region or domain in accordance with Kabat convention (Kabat, et al., Ann. NY Acad. Sci. 190:382-93 (1971); Kabat, et al., Sequences of Proteins of Immunological Interest, Fifth Edition, U.S. Department of Health and Human Services, NIH Publication No. 91-3242 (1991)). Each HCVR and LCVR is composed of three CDRs and four FRs, arranged from amino-terminus to carboxy-terminus in the following order: FR1-CDR1-FR2-CDR2-FR3-CDR3-FR4. The portion of an antibody consisting of LCVR and HCVR domains is designated Fv (Fragment variable) and constitutes the antigen-binding site. Single chain Fv (scFv) is an antibody fragment containing a LCVR domain and a HCVR domain on one polypeptide chain, wherein the N terminus of one domain and the C terminus of the other domain are joined by a flexible linker.

The term "human antibody" as used herein, includes antibodies having variable and constant regions corresponding to human germline immunoglobulin sequences (as described in Kabat, et al., supra).

Antibody specificity refers to selective recognition of the antibody for a particular epitope of an antigen. The specificity of the antibodies of the present invention for c-Kit can be determined based on affinity and/or avidity. Affinity, represented by the equilibrium constant for the dissociation of an antigen with an antibody ($K_D$), measures the binding strength between an antigenic determinant and an antibody-binding site. A surface plasmon resonance (SPR) biosensor such as the BIAcore® 3000 may be used to measure binding kinetics and affinity of the antibodies disclosed herein. The BIAcore® system utilizes the optical properties of SPR to detect alteration in protein concentration of interacting molecules within a dextran biosensor matrix. The binding kinetics of anti-c-Kit monoclonal antibodies including $K_D$ values can be determined by a SPR biosensor essentially as described in Example 4 below.

The phrase "specifically binds" as used herein in reference to the affinity of a c-Kit antibody for the ECD of c-Kit is intended to mean, unless indicated otherwise, a $K_D$ of less than about $2 \times 10^{-10}$ M, and, preferably, between about $2 \times 10^{-10}$ M and about $2 \times 10^{-12}$ M, as determined by common methods known in the art, including by use of a SPR biosensor essentially as described herein.

One aspect of this invention pertains to an antibody that specifically binds to the ECD of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6). In some embodiments, the antibodies of the present invention comprise a LCVR wherein the LCVR amino acid sequence is
AIQLTQSPSSLSASVGDRVTIT-CRASQGISSALAWYQQKPGKAPKLLIYDA SSLES-GVPSRFSGSGSGTDFTLTISSLQPEDFA-TYYCQQFNSYPLTFGGGTKVEIK (SEQ ID NO: 13), and a HCVR wherein the HCVR amino acid sequence is
QVQLVQSGAAVKKPGESLKISCKGSGYR-FTSYWIGWVRQMPGKGLEWM GIIYPGDSDTRYSPS-FQGQVTISAGKSISTAYLQWSSLKASD-TAMYYCARHGRGY NGYEGAFDIWGQGTMVTVSS (SEQ ID NO: 7).

In some embodiments, the antibodies of the present invention comprise a heavy chain and a light chain wherein the heavy chain amino acid sequence is SEQ ID NO: 9 and the light chain amino acid sequence is SEQ ID NO: 15.

In other embodiments, the antibodies of the present invention comprise two heavy chains and two light chains, wherein each of the heavy chain amino acid sequences is SEQ ID NO: 9 and each of the light chain amino acid sequences is SEQ ID NO: 15.

Another aspect of this invention pertains to an antibody that specifically binds to the ECD of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6), and wherein the antibody has at least one property selected from 1) inhibition of human c-Kit binding to human SCF; 2) complete antagonism of human c-Kit; 3) inhibition of SCF-dependent signaling pathways; 4) inhibition of SCF-independent activation of human c-Kit; 5) induction of human c-Kit internalization; 6) induction of human c-Kit degradation; 7) inhibition of tumor cell growth in vitro; 8) inhibition of tumor cell growth in vivo; and 9) binds to the ECD of human c-Kit with a $K_D$ less than about $2 \times 10^{-10}$ M. Preferably, such an antibody possesses at least two properties selected from 1) through 9). More preferably, such an antibody possesses at least three properties selected from 1) through 9). Even more preferably, such an antibody possesses at least four properties selected from 1) through 9). Even more preferably, such an antibody possesses at least five properties selected from 1) through 9). Most preferably, such an antibody possesses properties 1) through 9).

In some embodiments, the invention provides an antibody that specifically binds to the ECD of human c-Kit consisting of the amino acid sequence as in SEQ ID NO: 20 with a $K_D$ less than about $2 \times 10^{-10}$ M, preferably, between about $2 \times 10^{-10}$ M and about $2 \times 10^{-12}$ M, more preferably, between about 100 pM and about 5 pM, even more preferably, between about 100 pM and about 10 pM, even more preferably, between about 75 pM and about 25 pM, even more preferably, between about 75 pM and about 50 pM, or most preferably, between about 70 pM and about 60 pM, as determined by SPR at 25° C.

In some embodiments, the invention provides an antibody that specifically binds to the ECD of human c-Kit consisting of the amino acid sequence as in SEQ ID NO: 20, wherein binding of the antibody to the ECD of c-Kit induces internalization of c-Kit. Preferably, the binding of the antibody to the ECD of c-Kit receptor induces internalization of at least 50% of the c-Kit expressed on the surface of tumor cells after treatment of the tumor cell with about 1 µg/ml of said antibody for about 1 hour at 37° C. as determined by FACS in an in vitro assay of c-Kit internalization essentially as described in Example 6 below. More preferably, the binding of the antibody to the ECD of c-Kit receptor induces internalization of at least 75% of the c-Kit expressed on the surface of tumor cells after treatment of the tumor cell with about 1 µg/ml of said antibody for about 6 hours at 37° C. as determined by FACS in an in vitro assay of c-Kit internalization essentially as described in Example 6 below.

In some embodiments, the invention provides an antibody that specifically binds to the ECD of human c-Kit consisting of the amino acid sequence as in SEQ ID NO: 20, wherein binding of the antibody to the ECD of c-Kit induces degradation of the plasma membrane bound c-Kit expressed by tumor cells. Preferably, the binding of the antibody to the ECD of c-Kit induces degradation of at least 50% of plasma membrane bound c-Kit expressed by tumor cells after treatment of the tumor cells with about 100 ng/ml of said antibody for about 12 hours at 37° C. as determined by an in vitro assay of c-Kit degradation essentially as described in Example 7 below. More preferably, the binding of the antibody to the ECD of c-Kit induces degradation of at least 75% of the plasma membrane bound c-Kit expressed by tumor cells after treatment of the tumor cells with about 100 ng/ml of said antibody for about 24 hours at 37° C. as determined by an in vitro assay of c-Kit degradation essentially as described in Example 7 below.

In some embodiments, the invention provides an antibody that specifically binds to the ECD of human c-Kit consisting of the amino acid sequence as in SEQ ID NO: 20, wherein binding of the antibody to the ECD of c-Kit inhibits SCF-induced phosphorylation of c-Kit and/or MAPK in an in vitro tumor cell-based assay. Preferably, the c-Kit antibody inhibits SCF-induced phosphorylation of c-Kit and/or MAPK in an in vitro tumor cell-based assay with an $IC_{50}$ less than about 1 nM, more preferably, between about 1 nM and about 1 pM, even more preferably, between about 500 pM and about 5 pM, even more preferably, between about 500 pM and about 10 pM, even more preferably, between about 500 pM and about 100 pM, even more preferably, between about 500 pM and about 250 pM, or most preferably, about 300 pM.

In some embodiments, the invention provides an antibody that specifically binds to the ECD of human c-Kit consisting of the amino acid sequence as in SEQ ID NO: 20, wherein binding of the antibody to the ECD of c-Kit inhibits tumor cell growth in an in vivo assay performed essentially as described in Example 11 below. Preferably, binding of the antibody to the ECD of c-Kit inhibits tumor cell growth by at least about 30% in an in vivo assay performed essentially as described in Example 11 below. More preferably, binding of the antibody to the ECD of c-Kit inhibits tumor cell growth by at least about 50% in an in vivo assay performed essentially as described in Example 11 below. Even more preferably, binding of the antibody to the ECD of c-Kit inhibits a leukemia, small cell lung cancer, melanoma, gastrointestinal stromal tumor (GIST), Ewing's sarcoma, renal cancer, and/or neuroblastoma tumor cell growth by at least about 30%, or even more preferably, by at least about 60%, in an in vivo assay performed essentially as described in Example 11 below.

In one aspect, the invention provides a method for treating a disorder associated with increased ligand dependent or ligand independent c-Kit activity, said method comprising administering to a human in need of such treatment an effective amount of an antibody that specifically binds to the ECD of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6). In one embodiment, said disorder is cancer.

A "disorder" or "disease" is any condition that would benefit from treatment with an antibody or method of the invention. This includes chronic and acute disorders or diseases including those pathological conditions which predispose the human to the disorder in question. For example, disorders to be treated with the antibodies of the present invention include malignant and benign tumors; carcinoma, leukemia, blastoma, and sarcoma including, but not limited to, leukemia, small cell lung cancer, melanoma, GIST, Ewing's sarcoma, renal cancer, and neuroblastoma. Preferably, disorders to be treated with the antibodies of the present invention include c-Kit dependent malignant and benign tumors; cKit dependent carcinoma, leukemia, blastoma, and sarcoma, including, but not limited to, c-Kit dependent leukemia, small cell lung cancer, melanoma, GIST, Ewing's sarcoma, renal cancer, and neuroblastoma.

Another aspect of this invention pertains to a method of treating cancer in a human, comprising administering to said human in need of such treatment an effective amount of a c-Kit antibody of the invention, wherein the cancer is selected from the group consisting of leukemia, small cell lung cancer, melanoma, GIST, Ewing's sarcoma, renal cancer, and neuroblastoma. Preferably, the cancer is c-Kit dependent.

In one aspect, the invention provides a pharmaceutical composition comprising a one or more of the c-Kit antibodies of the invention together with at least one pharmaceutically acceptable carrier, diluent or excipient.

In one aspect, the invention provides a c-Kit antibody described herein for use in therapy.

In one aspect, the invention provides any of the c-Kit antibodies described herein for use in treating cancer.

In one aspect, the invention provides any of the c-Kit antibodies described herein for use in treating cancer wherein the cancer is selected from the group consisting of leukemia, small cell lung cancer, melanoma, GIST, Ewing's sarcoma, renal cancer, and neuroblastoma. Preferably, the cancer is c-Kit dependent.

In a further aspect, the invention provides the use of a c-Kit antibody described herein in the manufacture of a medicament for the treatment of a cancer, a tumor, and/or a cell proliferative disorder. Preferably, the cancer is c-Kit dependent.

In one aspect, the invention provides methods comprising administration of a therapeutically effective amount of a c-Kit antibody described herein in combination with an effective amount of another therapeutic agent (such as an anti-angiogenesis agent, another antibody, a chemotherapeutic agent, a cytotoxic agent, an immunosuppressive agent, a cytokine, cytotoxic radiotherapy, a corticosteroid, or an anti-emetic). For example, a c-Kit antibody described herein may be used in combination with one or more different anti-cancer and/or anti-angiogenic agents to treat various neoplastic or non-neoplastic conditions. In various embodiments, a c-Kit antibody of the invention may administered before, during, substantially simultaneously with, or after commencing therapy with one or more other therapeutic agents such as another anti-cancer agent. Preferably, at least one of the other anti-cancer agents is selected from the group consisting of imatinib, sunitinib, cytarabine (araC), dacarbazine (DTIC), cisplatin, and etoposide Another aspect of this invention pertains to isolated nucleic acid molecules encoding any of the aforementioned c-Kit antibodies, expression vectors comprising the nucleic acid molecules, and host cells comprising the nucleic acid molecules. The invention further provides methods of purifying any of the aforementioned c-Kit antibodies.

Another aspect of this invention pertains to an antibody that specifically binds to the ECD of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6) and wherein binding of the antibody induces c-Kit internalization and/or induces degradation of c-Kit and/or reduced phosphorylation of c-Kit and/or MAPK.

Another aspect of this invention pertains to an antibody that specifically binds to the ECD of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6), and wherein binding of the antibody inhibits tumor cell growth in vitro and/or reduces tumor cell growth in vivo.

Another aspect of this invention pertains to an antibody that specifically binds to the ECD of human c-Kit consisting of the amino acid sequence as in SEQ ID NO: 20, the antibody comprising a HCVR and a LCVR, wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6), and wherein binding of the antibody induces internalization and/or degradation of c-Kit and/or reduces phosphorylation of c-Kit and/or MAPK, inhibits tumor cell growth in vitro, and/or reduces tumor cell growth in vivo.

Preferred host cells for transformation of vectors and expression of the antibodies of the present invention are mammalian cells, e.g., NS0 cells (non-secreting (0) mouse myeloma cells), 293, SP20 and CHO cells and other cell lines of lymphoid origin such as lymphoma, myeloma, or hybridoma cells. Other eukaryotic hosts, such as yeasts, can be alternatively used.

An "isolated" antibody in reference to a c-Kit antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, an antibody of the present invention will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. The term "isolated" in reference to a c-Kit antibody of the present invention may include the antibody in situ within recombinant cells since at least one component of the antibody's natural environment will not be present. The c-Kit antibodies of the present invention may be isolated or purified by any method known in the art, including precipitation by ammonium sulfate or sodium sulfate followed by dialysis against saline, ion exchange chromatography, affinity or immuno-affinity chromatography including, but not limited to, Protein-A affinity chromatography, as well as gel filtration or zone electrophoresis.

Additionally, the present invention provides expression vectors containing the polynucleotide sequences previously described operably linked to a control sequence such as an expression sequence, a promoter and/or an enhancer sequence. A variety of expression vectors for the efficient synthesis of antibody polypeptide in prokaryotic systems, such as bacteria and eukaryotic systems, including but not limited to, yeast and mammalian cell culture systems have been developed. The vectors of the present invention can comprise segments of chromosomal, non-chromosomal and synthetic DNA sequences.

The present invention also provides recombinant host cells containing the recombinant vectors previously described. Antibodies of the present invention can be expressed in cell lines other than in hybridomas. Nucleic acids, which comprise a sequence encoding an antibody according to the invention, can be used for transformation of a suitable mammalian host cell.

Cell lines of particular preference are selected based on high levels of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells.

A method of treating tumor growth and/or cancer in a human by administering to the human an effective amount of a c-Kit antibody described herein is also provided by the present invention. Suitable conditions to be treated according to the present invention involve cells expressing human c-Kit. While not intended to be bound to any particular mechanism, the present methods provide for treatment of the growth of cancer cells including, for example, those in which neoplastic growth is c-Kit dependent.

"Treatment" or "treat", in the context of the present invention refers to therapeutic treatment including inhibiting, slowing, lessening or reversing the progress of the underlying condition or undesired physiological change associated with a disease or disorder, ameliorating clinical symptoms of a condition or preventing the appearance of clinical symptoms of the condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. Treatment can also mean prolonging survival as compared to expected survival if not receiving treatment. Those in need of treatment are those already with the disease. In one embodiment, the present invention can be used as a medicament.

In the methods of the present invention, a therapeutically effective amount of an antibody of the invention is administered to a human in need thereof. Additionally, the pharmaceutical compositions of the invention may include a therapeutically effective amount of a c-Kit antibody of the invention. A "therapeutically effective amount" or "effective dose" refers to an amount effective, at dosages and for periods of time necessary, to achieve the desired therapeutic result. A therapeutically effective amount of the antibody may vary according to factors such as the disease state, age, sex, and weight of the individual, and the ability of the antibody or antibody portion to elicit a desired response in the individual. Other factors include administration, target site, physiological state of the patient, whether the patient is human or an animal, other medications administered, and whether treatment is prophylactic or therapeutic. A therapeutically effective amount is also one in which any toxic or detrimental effects of the antibody or antibody portion are outweighed by the therapeutically beneficial effects. Although the c-Kit antibodies described herein are particularly useful for administration to humans, they can be administered to other mammals as well for therapeutic purposes.

Dosage regimens may be adjusted to provide the optimum desired response (e.g., a therapeutic or prophylactic response). Treatment dosages may be titrated using routine methods known to those of skill in the art to optimize safety and efficacy. Dosing schedules will typically range from a single bolus dosage or continuous infusion to multiple administrations per day (e.g., every 4-6 hours), or as indicated by the treating physician and the patient's condition. Dosing amounts and frequencies will be determined by the physicians treating the patient. It should be noted, however, that the present invention is not limited to any particular dose.

Anti-c-Kit antibodies of the invention can be administered in combination with an anti-neoplastic agent including, but not limited to, cytarabine (i.e., araC), dacarbazine (DTIC), cisplatin, or etoposide.

In the present invention, any suitable method or route can be used to administer c-Kit antibodies of the invention, and optionally, to co-administer anti-neoplastic agents and/or antagonists of other receptors. In a combination therapy of the present invention, the c-Kit antibody can be administered before, during, substantially simultaneous with, or after commencing therapy with another agent.

The c-Kit antibodies of the invention, where used for the purpose of therapeutic treatment, are preferably formulated as pharmaceutical compositions. Such pharmaceutical compositions and processes for preparing the same are well known in the art. See, e.g., Remington: The Science and Practice of Pharmacy (A. Gennaro, et al., eds., 21st ed., Mack Publishing Co., 2005).

Example 1

Human Monoclonal Antibodies Against Human c-Kit

The amino acid sequences of the CDRs of the anti-human c-Kit mAb, CK6, are shown in Table 1.

TABLE 1

|  | CK6 HC | CK6 LC |
| --- | --- | --- |
| CDR1 | SYWIG (SEQ ID NO: 1) | RASQGISSALA (SEQ ID NO: 4) |
| CDR2 | IIYPGDSDTRYSPSFQG (SEQ ID NO: 2) | DASSLES (SEQ ID NO: 5) |
| CDR3 | HGRGYNGYEGAFDI (SEQ ID NO: 3) | CQQFNSYPLT (SEQ ID NO: 6) |

The SEQ ID NOs depicting the amino acid sequences of the CK6 mAb HCVR, LCVR, heavy chain (HC), and the light chain (LC) and the cDNA sequences encoding them are provided in Table 2 below.

TABLE 2

|  | CK6 | |
| --- | --- | --- |
|  | Amino acid Sequence | DNA Sequence |
| HCVR | SEQ ID NO: 7 | SEQ ID NO: 8 |
| LCVR | SEQ ID NO: 13 | SEQ ID NO: 14 |
| HC | SEQ ID NO: 9 | SEQ ID NO: 10 |
| LC | SEQ ID NO: 15 | SEQ ID NO: 16 |
| HC | SEQ ID NO: 11* | SEQ ID NO: 12** |
| LC | SEQ ID NO: 17* | SEQ ID NO: 18** |

*Sequence include amino acid sequence of secretory signal peptide.
**Sequence includes nucleotide sequence encoding the secretory signal peptide Example 2

Expression and Purification of Human IgG1 Anti-Human c-Kit Monoclonal Antibodies The cDNA sequences encoding a heavy chain variable region and a light chain variable region of an anti-c-Kit mAb may be amplified by PCR for cloning into expression vectors according to procedures known in the art. For example, the cDNA encoding the heavy chain variable region (e.g., SEQ ID NO: 8) may be fused in frame to the cDNA sequence encoding human immunoglobulin heavy chain gamma1 constant region in vector pEE6.1 (Lonza Biologics plc, Slough, Berkshire, UK). The cDNA encoding the entire human light chain (e.g., SEQ ID NO: 16) may be cloned directly into vector pEE12.1 (Lonza Biologics PLC, Slough, Berkshire, UK). The engineered immunoglobulin expression vectors may be stably transfected in NS0 myeloma cells by electroporation and transfectants cultured in glutamine synthetase selection medium. Stable clones may be screened for antibody expression by anti-human c-Kit specific binding ELISA. Positive clones may be cultured into serum-free medium culture for antibody production in spinner flasks or bioreactors. Full length IgG1 antibody may be purified by protein affinity chromatography (Poros A, PerSeptive Biosystems Inc., Foster City, Calif.) and eluted into a neutral buffered saline solution.

Alternatively, the cDNA sequences encoding a heavy chain variable region and light chain variable region of an anti-human c-Kit mAb (e.g., SEQ ID NOs: 8 and 14, respectively) may be cloned and fused in frame to the cDNA sequence encoding a human immunoglobulin heavy chain gamma1 constant region in a GS (glutamine synthetase) expression vector. The engineered immunoglobulin expression vectors may be stably transfected in CHO cells. Stable clones may be verified for expression of an antibody specifically binding to human c-Kit. Positive clones may be expanded into serum-free medium culture for antibody production in bioreactors. Full length IgG1 antibody may be purified by protein A affinity chromatography and eluted into a neutral buffered saline solution.

Example 3

In Vitro Binding and Blocking Activities of Anti-Human c-Kit Monoclonal Antibody, CK6

The in vitro c-Kit binding and blocking activities of purified anti-c-Kit mAbs can be determined using immunological, quantitative techniques known in the art such as an enzyme-linked immunosorbent assay (ELISA), for example. Briefly, 96-well microtiter plates are coated with 100 µl/well of 1 µg/ml recombinant human c-Kit (rh-c-Kit) protein (R&D Systems, Minneapolis, Minn.) at room temperature (20-25° C.) for one hour. Following washes, wells are blocked with 3% PBS/milk. Different dilutions of purified anti-c-Kit mAbs, typically starting at 1.5 µg/ml or 100 nM, are then added to the rh-c-Kit-coated wells and allowed to incubate for two hours at room temperature. Following several washes (3-5), a 1:1000 dilution of anti-human IgG-HRP conjugated antibody (Jackson ImmunoResearch, West Grove, Pa.) is added to the plates for one hour at room temperature. Plates are washed and HRP substrate is added to each well and incubated until blue color is developed. Stop solution is added and absorbance is measured at 450 nm. The monoclonal antibody CK6 was tested for binding to rh-c-Kit protein in an ELISA as described above. Results indicate that CK6 binds to rh-c-Kit with $EC_{50}$ values of about $3 \times 10^{-11}$ M.

Purified mAbs can be also tested for their ability to block the binding of c-Kit and its ligand. Briefly, 96-well microtiter plates are coated with 100 µl/well of 1 µg/ml c-Kit ligand stem cell factor (SCF) (R&D Systems), at room temperature for one hour. Following washes, wells are blocked with 3% PBS/milk. Different dilutions of mAbs (typically starting at 15 µg/ml or 1.0 µM) are first incubated for one hour at room temperature with rh-c-Kit (R&D Systems) and then added to the SCF-coated wells for additional incubation at room temperature for two hours. Following several washes (3-5), a 1:1000 dilution of anti-human IgG-HRP conjugated antibody is added to the plates for one hour at room temperature. Plates are washed in 0.2% Tween-PBS and HRP substrate is added to each well and incubated until blue color is developed. Stop solution is added and absorbance is measured at 450 nm.

The monoclonal antibody CK6 was tested for the ability to block the binding of c-Kit and its ligand in the above assay. The results indicate that CK6 blocks c-Kit-ligand interaction with an $IC_{50}$ value of about $4 \times 10^{-11}$ M.

Example 4

Binding Kinetics of Anti-c-Kit Monoclonal Antibody, CK6

The binding kinetics of anti-c-Kit monoclonal antibodies to rh-c-kit can be determined by a SPR biosensor such as a BIAcore® 3000 or BIAcore® T100 (GE Health Care, Piscataway, N.J.) according to methods known in the art. Essentially, anti-cKit monoclonal antibodies may be assessed with SPR using the BIAcore® T100 and HBS-EP (0.01 M HEPES-pH 7.4, 0.15 mM NaCl, 3 mM EDTA and 0.005% (v/v) surfactant P20) as a running buffer during binding affinity measurements. Measurements are performed at 25° C. Around 120 response units (RU) of rh-c-kit (pH 5.0) may be immobilized onto a CM5 chip using the standard amine coupling procedure. The mAbs may be injected for 180 seconds over immobilized rh-c-kit at a flow rate of about 30 μL/min, followed by 900 seconds dissociation using HBS-EP. Concentrations of anti-c-Kit monoclonal antibodies may be gradients of 2-fold dilutions, with at least three concentrations per gradient, and three gradients per experiment. After dissociation, regeneration of the rh-c-kit surface may be achieved with two 30 seconds injections of 50 mM HCl at 30 μl/min. BIAcore® T100 evaluation software may be used to determine rate constants. The affinity constant, $K_D$, may be calculated from the ratio of the rate constants $K_{off}/K_{on}$. The "$K_{on}$, $M^{-1}s^{-1}$" and "$K_{off}$, $s^{-1}$", rates of the interaction is used to determine the affinity ($K_D$, M) of the antibody/receptor interaction.

The monoclonal antibody CK6 was tested for its binding kinetics to human c-Kit protein. The measurements were obtained at 25° C. The $K_D$, $K_{on}$, and $K_{off}$ rates for mAb CK6 are presented in Table 3.

TABLE 3

|  | $K_D$ (M) | $K_{on}$ (1/Ms) | $K_{off}$ (1/s) |
|---|---|---|---|
| CK6 | $6.6 \times 10^{-11}$ | $2.3 \times 10^6$ | $1.5 \times 10^{-4}$ |

Example 5

Species Specificity of Anti-Human c-Kit Monoclonal Antibody, CK6

The species binding specificity of anti-human c-Kit mAbs can be determined by measuring the reactivity of the antibodies to human, cynomolgus, and mouse c-Kit proteins in an ELISA. Briefly, 96-well microtiter plates are coated with 100 μl/well of 1 mg/ml recombinant human c-Kit protein (rh-c-Kit) or recombinant mouse c-Kit (rm-c-Kit; Gln26-Thr519) obtained commercially (R&D Systems), or cynomolgus c-Kit (cyno-c-Kit; Met1-His549 prepared recombinantly) at room temperature for one hour. Following washes, wells are blocked with 3% PBS/milk. Serial dilutions of human anti-human-c-Kit mAbs are then added to the c-Kit-coated wells and allowed to incubate for two hours at room temperature. Following several washes, a 1:1000 dilution of anti-human IgG-HRP conjugated antibody is added to the plates for one hour at room temperature in order to detect bound human antibody. Plates are washed and HRP substrate is added to each well and incubated until blue color is developed. Stop solution is added and absorbance is measured at 450 nm. The results show that CK6 binds to rh-c-Kit, cynomologus c-Kit (with $EC_{50}$ of $5.7 \times 10^{-11}$ M) but does not bind significantly to rm-c-Kit (Table 4).

TABLE 4

CK6 Ab Binding to human and mouse c-Kit (ELISA)

| Antibody | Binding (HRP-LM1 450 nm) | | | |
|---|---|---|---|---|
| CK6 [ng/ml] | human c-Kit (1.0 μg/ml) | | mouse c-Kit (1.0 μg/ml) | |
| 10000 | 1.9532 | 1.9444 | 0.0537 | 0.0983 |
| 3000 | 1.8952 | 1.8696 | 0.051 | 0.0581 |
| 1000 | 1.9523 | 1.8683 | 0.0551 | 0.0533 |
| 300 | 1.817 | 1.7809 | 0.0549 | 0.0509 |
| 100 | 1.6891 | 1.6215 | 0.0654 | 0.0794 |
| 30 | 1.2876 | 1.4092 | 0.0512 | 0.0569 |
| 10 | 0.7616 | 0.7445 | 0.0557 | 0.056 |
| 3 | 0.3378 | 0.3495 | 0.0547 | 0.0548 |
| 1 | 0.1486 | 0.153 | 0.0721 | 0.0582 |
| 0.3 | 0.1066 | 0.1064 | 0.0546 | 0.0508 |
| 0.1 | 0.0613 | 0.0604 | 0.0496 | 0.0528 |
| 0.03 | 0.0534 | 0.0492 | 0.0483 | 0.0535 |

TABLE 5

CK6 Ab Binding to human and cynomolgus c-Kit (ELISA)

| Antibody | Binding (HRP-LM1 450 nm) | | | |
|---|---|---|---|---|
| CK6 (ng/ml) | human c-Kit (1.0 μg/ml) | | cynomolgus c-Kit (1.0 μg/ml) | |
| 15000.00 | 1.1747 | 0.8256 | 1.3142 | 1.2592 |
| 5000.00 | 1.1952 | 1.1108 | 1.4176 | 1.2885 |
| 1666.67 | 1.2093 | 1.1712 | 1.3205 | 1.3004 |
| 555.56 | 1.1296 | 1.1664 | 1.223 | 1.3557 |
| 185.19 | 1.1012 | 1.1515 | 1.2084 | 1.3166 |
| 61.73 | 1.0697 | 0.9272 | 0.9891 | 0.8668 |
| 20.58 | 0.4112 | 0.6486 | 0.5567 | 0.609 |
| 6.86 | 0.1646 | 0.3458 | 0.257 | 0.5014 |
| 2.29 | 0.1411 | 0.2687 | 0.2103 | 0.3951 |
| 0.76 | 0.0519 | 0.0419 | 0.0507 | 0.0448 |

Species specificity of c-Kit mAbs can be further tested for their binding to plasma membrane bound c-Kit expressed on the surface of human Mo7e and mouse P815 cells based on the flow cytometry analysis (see, e.g., WO2004/007735). Briefly, whole, live human Mo7e and mouse P815 cells are serum starved overnight, washed 3 times in cold blocking buffer (5% FBS in PBS), and then resuspended in 100 μl of blocking buffer. An anti-c-Kit antibody is added at 1.0 μg/ml and the mixture is incubated for 30 minutes at 4° C. A secondary fluorescence-conjugated antibody (Jackson ImmunoResearch) is added at 1.0 μg/ml to detect human antibody bound to the cell surface via flow cytometry analysis. Results show that CK6 binds to plasma membrane bound human c-Kit expressed by human tumor cells (i.e., Mo7e), but not to plasma membrane bound mouse (p815) c-Kit expressed by mouse tumor cells (i.e., p815) in a cell-based assay.

TABLE 6

Human and Mouse c-Kit Expressing Cell Lines (FACS)

| Cell Line | Species | Antibody | Mean Fluorescence (HLog) | Comments |
|---|---|---|---|---|
| Mo7e | Human | PE Only | 6.00E+00 | Background |
| Mo7e | Human | CK6 | 8.00E+02 | Ab Binding |
| p815 | Mouse | PE Only | 4.00E+00 | Background |
| p815 | Mouse | CK6 | 7.00E+00 | Ab Binding |

Species specificity of c-Kit mAbs can be further tested by measuring the binding of the mAbs to plasma membrane bound c-Kit expressed on the surface of isolated cynomolgus bone marrow cells. Briefly, bone marrow in a DPBS suspension is layered over a Histopaque 1077 density gradient to separate blood components. After centrifugation, white blood cells are harvested from the interface and quickly rinsed in ACK lysis buffer to remove any remaining red blood cells. The isolated leukocytes are then labeled with CK6, followed by a phycoerythrin-conjugated anti-human IgG secondary antibody and subjected to FACS analysis.

TABLE 7

FACS analysis of cynomolgus bone marrow cells for c-Kit expression

| Cells | Species | Antibody | Mean Fluorescence (HLog) | Comments |
|---|---|---|---|---|
| Bone Marrow | cynomolgus | PE Only | 1.80E+01 | Background |
| | | CK6 | 2.00E+02 | mAb Binding |

FACS analysis of cynomolgus bone marrow cells for c-Kit expression using CK6 mAb indicates that CK6 binds plasma membrane bound cynomolgus c-Kit expressed on the cell surface of bone marrow cells.

Example 6

In Vitro c-Kit Internalization Assays

An in vitro cell based assay may be used to measure the neutralization activity of c-Kit mAbs directed against human c-Kit expressing cells. Such an assay may be based on c-Kit mAb-induced internalization may employ fluorescence-activated cell sorting (FACS) analysis as briefly described below.

Serum-starved, c-Kit expressing Mole cells at a concentration of $1 \times 10^6$ cells/ml are incubated at 4° C. for 1 hour. Anti-c-Kit antibody is added to cells at a concentration of 1 µg/ml incubated for different time intervals at 4° C. and 37° C. Cells are washed 3 times in 200 µl blocking buffer (5% Fetal Bovine Serum in PBS) to remove any unbound antibody. Cells are resuspended in 100 µl blocking buffer. A phycoerythrin-conjugated anti-human IgG-Fc-gamma antibody (Jackson ImmunoResearch) is added to detect the presence of bound antibody and to cells without previous antibody exposure as a negative control. Cells are kept in the dark when possible from this point on. Cells are incubated for 30 minutes at 4° C. and washed as before. Cell samples are then run through a multi-color detection assay system (e.g., Guava easyCyte System (Millipore, Billerica, Mass.)) which detects fluorescence-labeled cells.

The mean fluorescence intensity on the cell surface reflects the quantity of c-Kit molecules that remain on the cell surface after treatment with the c-Kit antibody. The data from a representative experiment shows a time-dependent reduction of cell surface c-Kit after 1 hour, 6 hours and 24 hours incubation of cells with anti-c-Kit mAb CK6 at 37° C. (see Table 8). Incubation of cells with CK6 at 4° C. resulted in a non-significant change in c-Kit content (negative control). These data show that the anti-c-Kit mAb CK6 dramatically induces internalization of c-Kit in cells expressing c-Kit in vitro.

TABLE 8

In vitro CK6-induced internalization of c-Kit

| Treatment | Temp (° C.) | Time (hr) | Detection Antibody | Mean Fluorescence (HLog) | Comments |
|---|---|---|---|---|---|
| NA | 4 | 24 | anti-hIgG-PE | 3.00E+00 | Baseline |
| CK6 | 37 | 24 | anti-hIgG-PE | 2.00E+01 | 99% reduction |
| CK6 | 37 | 6 | anti-hIgG-PE | 7.00E+02 | 82% reduction |
| CK6 | 37 | 1 | anti-hIgG-PE | 2.00E+03 | 50% reduction |
| CK6 | 4 | 24 | anti-hIgG-PE | 4.00E+03 | Control |
| NA | 4 | 24 | CK6 + anti-hIgG-PE | 6.50E+03 | Control |

Example 7

In Vitro c-Kit Degradation Assay

An in vitro cell based assay may be used to measure the ability of c-Kit mAbs to induce degradation of c-Kit as measured by the amount of total c-Kit found in cell lysates after treating tumor cells with a c-Kit mAb at 37° C. Briefly, human cell lines expressing c-Kit (e.g., Mo7e and GIST882) are plated in a 6-well dish at a density of $3 \times 10^6$ cells/ml in 3 ml of serum-free media. CK6 antibody (100 ng/ml) is added to the wells and incubated at 37° C. for 48, 24, and 12 hours. One well of cells is left untreated as a control. Immediately after the treatment period, the cells are washed in cold PBS, lysed in 100 µl lysis buffer (50 mM Hepes pH 7.5, 150 mM NaCl, 10 mM NaPPi, 50 mM NaF, 1 mM $Na_3VO_4$, 1% Triton X-100, protease inhibitor cocktail). After a ten minute incubation on ice, the cells are centrifuged at 12,000 g for 15 minutes at 4° C. The supernatant is collected and subjected to western blot analysis under reducing conditions. The blot is probed with an anti-human c-Kit antibody (Invitrogen, Carlsbad, Calif.; catalog #34-8800) to detect the amount of whole c-Kit in the cells before and after incubation with CK6 for varying amounts of time. The results show significant degradation of c-Kit compared to untreated cells after 12 hours of incubation with c-Kit mAb, CK6 (Table 9). The CK6 induced degradation of c-Kit increases in a time-dependent manner. As expected from previous reports in the scientific literature, degradation of c-Kit was not observed after treatment of the tumor cells with SCF (100 ng/ml) for 12, 24, and 48 hours at 37° C. (data not shown).

TABLE 9

In vitro CK6-induced degradation of c-Kit

| Time (hrs) | Cell Line | WB c-Kit Level | Change | % Change/Baseline |
|---|---|---|---|---|
| 0 | GIST | 32 | 0 | Baseline-0% |
| 12 | | 9 | −23 | −71.88% |
| 24 | | 7 | −25 | −78.13% |
| 48 | | 5 | −27 | −84.38% |
| 0 | Mo7e | 53 | 0 | Baseline-0% |
| 12 | | 25 | −28 | −52.83% |
| 24 | | 21 | −32 | −60.38% |
| 48 | | 13 | −40 | −75.47% |

Example 7a

In Vitro c-Kit Degradation Assay

Human cell lines expressing c-Kit (e.g., GIST882, Mo7e, and Malm-3M) are plated in a 6-well dish at a density of $3\times10^6$ cells/ml in 3 ml of serum-free media for all but one Mo7e assay that uses 10% serum. CK6 antibody or SCF at various concentrations is added to the wells and incubated at 37° C. for 24 or 48 hours. One well of cells is left untreated as a control. Immediately after the treatment period, the cells are washed in cold PBS, lysed in 100 µl lysis buffer (50 mM Hepes pH 7.5, 150 mM NaCl, 10 mM NaPPi, 50 mM NaF, 1 mM $Na_3VO_4$, 1% Triton X-100, protease inhibitor cocktail). After a ten minute incubation on ice, the cells are centrifuged at 12,000 g for 15 minutes at 4° C. The supernatant is collected and subjected to western blot analysis under reducing conditions. The blot is probed with an anti-human c-Kit antibody (Invitrogen, Carlsbad, Calif.; catalog #34-8800 or Cell Signaling Technology, Danvers, Mass.; catalog#3308) to detect the amount of whole c-Kit in the cells before and after incubation with CK6 or SCF. The results show no significant degradation of c-Kit compared to untreated cells after incubation with c-Kit mAb, CK6. Degradation of c-Kit is observed after treatment of Mo7e tumor cells with SCF (1 ug/ml and 100 ng/ml) for 24 hours at 37° C. when using 0% serum. SCF induced degradation is not apparent when using 10% serum. (Replicates of GIST882=1, Mo7e=3, and Malm-3M=1). To demonstrate equivalent protein loading the blot is re-probed with an anti-GAPDH antibody (Ambion, Carlsbad, Calif.; catalog#AM4300).

Example 8

Identification of c-Kit-Dependent Human Cancer Cell Lines

Due to the lack of c-Kit expression across most adult tissue, the detection of c-Kit expression within a tumor usually suggests c-Kit-dependent cell growth. Human cancer-derived cell lines can be tested for c-Kit expression using flow cytometry analysis followed by c-Kit related cell-based phosphorylation and viability assays.

Briefly for c-Kit expression via flow cytometry analysis $1.0\times10^6$ whole, live cells are serum starved overnight, washed 3 times in blocking buffer (5% Fetal Bovine Serum in PBS), and then resuspended in 100 µl of blocking buffer. An anti-c-Kit antibody or control antibody is added at 1.0 µg/ml and the mixture is incubated for 30 minutes at 4° C. Cells are washed as before to remove any excess or unbound antibody. Cells are again resuspended in 100 µl blocking buffer and then incubated with a fluorescence-labeled secondary antibody to detect the first antibody bound to the cells. Cells are incubated for 30 minutes at 4° C. and kept in the dark once the fluorescence-labeled antibody is added. Cells are washed as previously to remove any unbound antibody and resuspended in 100 µl blocking buffer. Cell samples, which may include irrelevant antibody control samples, are then run through a multi-color detection assay system (e.g., Guava easyCyte System (Millipore, Billerica, Mass.)) which detects fluorescence-labeled cells. The mean fluorescence intensity on the cell surface reflects the quantity of c-Kit molecules on the cell surface compared to irrelevant antibody controls.

For c-Kit expression via Western blot $3.0\times10^6$ cells are serum starved overnight then washed in cold PBS. Cells are lysed in 100 µl ice-cold lysis buffer (50 mM Hepes pH 7.5, 150 mM NaCl, 10 mM NaPPi, 50 mM NaF, 1 mM $Na_3VO_4$, 1% Triton X-100, protease inhibitor cocktail) for 10 minutes on ice. Cell debris is pelleted by centrifugation at 12,000 rpm at 4° C. for 15 minutes. The supernatant is collected and subjected to western blot analysis under reducing conditions. The blot is probed with an anti-human c-Kit antibody (R&D Systems) and appropriate HRP-labeled secondary antibody to detect the amount of c-Kit present in the cells.

c-Kit status can be determined by lysing cells as described above after treatment with and without stimulation with the c-Kit ligand SCF (Peprotech, N.J.). The cell lysate is subject to Western blot analysis using an antibody probe specific for phosphorylated c-Kit. The presence of bands in the blot for both unstimulated and stimulated cells indicates either that there is an activating mutation in c-Kit whereby the c-Kit is phosphorylated even in the absence of its ligand or the cell line is producing its own ligand in an over expressing loop. Cell lines that are phosphorylated only in the presence of ligand are over expressing wild-type (WT).

TABLE 10

| Line | Origin | c-Kit Status |
| --- | --- | --- |
| TF-1 | Erythroleukemia | Over expressing WT |
| Mo7e | Megakaryocytic | Over expressing WT |
| EOL-1 | Eosinophilic | Over expressing WT |
| HEL | Erythroleukemia | Over expressing WT |
| OCI-M1 | Erythroleukemia | Over expressing WT |
| CMK | Megakaryocytic | Over expressing WT |
| OCI-AML5 | AML | Activating Mutation |
| GDM1 | AML | Activating Mutation |
| NCI-H526 | SCLC | Over expressing loop |
| NCI-H378 | SCLC | Over expressing loop |
| SK-N-MC | Neuroblastoma | Over expressing WT |
| RDES | Ewing's Sarcoma | Over expressing loop |
| TC32 | Ewing's Sarcoma | Over expressing loop |
| CADO-ES1 | Ewing's Sarcoma | Over expressing loop |
| MHH-ES1 | Ewing's Sarcoma | Over expressing loop |
| GIST882 | GIST | Activating Mutation |
| LN04 | GIST | Activating Mutation |
| T1 | GIST | Activating Mutation |
| RT4 | Bladder | Over expressing WT |
| RC29 | Renal | Over expressing WT |
| MALM-3M | Melanoma | Over expressing WT |
| WM39 | Melanoma | Over expressing WT |

Based on an analysis conducted essentially as described in this Example, fifteen cell lines derived from leukemia, melanoma, SCLC, Ewing's Sarcoma and GIST were determined to be c-Kit-dependent (see Table 10). The c-Kit status for each cell line was confirmed by a literature search and sequence analysis.

Example 9

In Vitro c-Kit and MAP Kinase Phosphorylation Assays

Interaction of SCF with c-Kit induces c-Kit dimerization, resulting in auto-phosphorylation of tyrosine residues of the cytoplasmic domain. Downstream of c-Kit, multiple signal transduction components are activated, including phosphatidylinositol-3-kinase, Src family members, the JAK/STAT pathway and the Ras-Raf-MAP kinase (MAPK) cascade.

The ability of anti-human c-Kit mAbs to inhibit c-Kit and MAPK phosphorylation in response to SCF may be determined in an in vitro cell-based assay according to the following procedure. Briefly, as described above in Example 8, c-Kit-dependent cell lines are serum starved overnight. They are then incubated with different dilutions of anti-c-Kit mAbs, typically ranging from 100 nM to 0.1 nM, for one hour at 37° C. Cells are then stimulated with 5 ng/ml SCF (R&D Systems or Peprotech) for 15 minutes at 37° C. Cells are then immediately washed in cold PBS and lysed in 100 µl ice-cold lysis buffer (50 mM Hepes pH 7.5, 150 mM NaCl, 10 mM NaPPi, 50 mM NaF, 1 mM $Na_3VO_4$, 1% Triton X-100, protease inhibitor cocktail) for 10 minutes on ice in order to extract cellular proteins. Cell debris is pelleted by centrifugation at 12,000 rpm at 4° C. for 15 minutes. The supernatant is collected and subjected to western blot analysis under reducing conditions. The blot is probed with phospho-specific anti-human c-Kit or MAPK antibody and an appropriate HRP-labeled secondary antibody to detect the level of phosphorylation of c-Kit and MAP kinase under our experimental conditions.

The monoclonal antibody CK6 was tested for its ability of inhibiting c-Kit and MAPK phosphorylation in response to SCF in Mo7e leukemia cells. The $IC_{50}$ of mAb CK6 in the phosphorylation inhibition assay is determined to be 300 pM. These results demonstrate that anti-c-Kit mAb CK6 can effectively block c-Kit activation and its downstream signaling.

Example 10

In Vitro Tumor Cell Growth Inhibition Assays

The inhibition of tumor cell growth by c-Kit monoclonal antibodies of the present invention may be examined in in vitro assays using any one of many commercially available cell viability assay kits. More specifically, the ability of CK6 to inhibit tumor cell growth was tested using a commercially available cell viability kit (e.g., CellTiter-Glo® Luminescent Cell Viability Assay, Promega, Madison, Wis., USA) according to the manufacturer's instructions.

Anti-c-Kit monoclonal antibody CK6 was determined to inhibit the cell viability of Mole cells with an $IC_{50}$ of about 300 pM (data not shown) as determined by use of the CellTiter-Glo® Luminescent Cell Viability Assay kit.

Example 11

In Vivo Tumor Cell Growth Inhibition Assays

The anti-tumor efficacy of the anti-c-Kit antibodies of the present invention may be further examined in relevant in vivo xenograft models essentially as known and widely used in the art.

Briefly described, c-Kit-dependent human cancer cell lines are expanded in culture and then are injected subcutaneously into the rear flank of athymic nude mice (Charles River, Wilmington, Mass.) with 2-10 million cells per mouse. Anti-c-Kit mAbs are diluted in PBS, pH 7.2, and administered by intravenous injection at 4 or 40 mg/kg. When tumor size has reached about 180-360 mm³, the mice are randomized and divided into control (for example, USP saline at 10 µl/g) and treatment groups (for example, mAb CK6 at 4 or 40 mg/kg). Furthermore, treatment groups may include appropriate chemotherapy drugs or approved RTK inhibitors alone or in combination with the antibodies of the present invention. Antibodies and saline control are administered three times per week for four weeks Inhibition of tumor cell growth is determined by three dimensional caliper measurement of tumor volume twice weekly during the course of treatment. Tumor volume may be calculated as follows:

$$\text{Tumor volume(mm}^3) = (\text{length of the tumor})(\text{width}^2 \text{ of the tumor})(\pi/6),$$

where the length of the tumor is the largest dimension of the tumor parallel to the skin surface and the width is the largest measurement perpendicular to the length, parallel to the skin surface. Body weight may also be measured frequently during the course of treatment as a general measurement of toxicity. T/C %, and P values are calculated by RM ANOVA where, $$T/C\% = [(\text{Treatment Volume/Initial Volume})/(\text{Control Volume/Initial Volume})] * 100$$

and the P value is calculated in relation to saline.

The data from various c-Kit relevant xenograft models using CK6 as a treatment are shown in Tables 11-14.

TABLE 11

CK6 as a monotherapy in xenograft assays using various human tumor cell lines

| | CK6 (4 mg/kg) | | (CK6 40 mg/kg) | |
|---|---|---|---|---|
| Cell Line | T/C % | P value | T/C % | P value |
| HEL | 83 | 0.3270 | 69 | 0.0208 |
| OCI-M1 | 66 | 0.0991 | 39 | 0.0033 |
| CMK | 86 | 0.1886 | 62 | 0.2789 |
| NCI-H526 | 96 | 0.5415 | 58 | 0.0121 |
| RDES | Not Tested | Not Applicable | 37 | 0.0441 |
| GIST882 | Not Tested | Not Applicable | 52 | 0.001 |
| RT4 | Not Tested | Not Applicable | 58 | 0.02 |
| RC29 | Not Tested | Not Applicable | 49 | 0.0145 |
| MALM-3M | Not Tested | Not Applicable | 36 | <0.0001 |

TABLE 12

CK6 as a mono- or combi- therapy in a xenograft assay using a human leukemia cell line

| | CK6 (40 mg/kg) | | AraC (5 mg/kg) | | CK6 (40 mg/kg)+ AraC (5 mg/kg) | |
|---|---|---|---|---|---|---|
| Cell Line | T/C % | P value | T/C % | P value | T/C % | P value |
| OCI-M1 | 60 | 0.0001 | 91 | 0.0021 | 47 | 0.0001 |

TABLE 13

CK6 as a mono- or combi- therapy in a xenograft assay using a human melanoma cell line

| | CK6 (40 mg/kg) | | DTIC (80 mg/kg) | | CK6 (40 mg/kg) + DTIC (80 mg/kg) | |
|---|---|---|---|---|---|---|
| Cell Line | T/C % | P value | T/C % | P value | T/C % | P value |
| Malm-3M | 58 | 0.0001 | 68 | 0.0021 | 38 | 0.0001 |

| | CK6 (40 mg/kg) | | Imatinib (100 mg/kg) | | Sunitinib (40 mg/kg) | |
|---|---|---|---|---|---|---|
| | T/C % | P value | T/C % | P value | T/C % | P value |
| Malm-3M | 43 | 0.0001 | 61 | 0.0001 | 68 | 0.0004 |

TABLE 14

CK6 as a mono- or combi- therapy in a xenograft assay using a human small cell lung cancer cell line

| Cell Line | CK6 (40 mg/kg) | | Cisplatin (5 mg/kg) + etoposide (40 mg/kg) | | CK6 (40 mg/kg) + Cisplatin (5 mg/kg) + etoposide (40 mg/kg) | |
|---|---|---|---|---|---|---|
| NCI-H526 | T/C % | P value | T/C % | P value | T/C % | P value |
| | 50 | 0.0001 | 38% | P < 0.0001 | 12% | P < 0.0001 |

These data demonstrate that the anti-c-Kit mAb CK6 dramatically inhibits tumor cell growth in various c-Kit relevant xenograft models. Treatment with CK6 demonstrated stronger anti-tumor activity as compared to standard anti-cancer agents such as cytarabine (araC) and dacarbazine (DTIC), as well as cisplatin in combination with etoposide. Furthermore, the combination of CK6 with DTIC or AraC demonstrated stronger anti-tumor activity as compared to mono-therapy. Likewise, the combination of CK6 with cisplatin and etoposide demonstrated stronger anti-tumor activity as compared to the cisplatin and etoposide combination alone.

We claim:

1. An antibody that specifically binds to the extracellular domain (ECD) of human c-Kit consisting of the amino acid sequence as in SEQ ID NO: 20, the antibody comprising a heavy chain variable region (HCVR) and a light chain variable region (LCVR), wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6).

2. The antibody of claim 1, wherein the LCVR amino acid sequence is SEQ ID NO: 13 and the HCVR amino acid sequence is SEQ ID NO: 7.

3. The antibody of claim 2 comprising a heavy chain and a light chain, wherein the heavy chain amino acid sequence is SEQ ID NO: 9 and the light chain amino acid sequence is SEQ ID NO: 15.

4. The antibody of claim 3 comprising two heavy chains and two light chains, wherein each of the heavy chain amino acid sequences is SEQ ID NO: 9 and each of the light chain amino acid sequences is SEQ ID NO: 15.

5. An antigen-binding fragment of an antibody that specifically binds to the extracellular domain (ECD) of human c-Kit consisting of the amino acid sequence as in SEQ ID NO: 20, the antibody comprising a heavy chain variable region (HCVR) and a light chain variable region (LCVR), wherein the HCVR comprises CDRH1, CDRH2, and CDRH3 amino acid sequences, and the LCVR comprises CDRL1, CDRL2, and CDRL3 amino acid sequences, wherein CDRH1 is SYWIG (SEQ ID NO: 1), CDRH2 is IIYPGDSDTRYSPSFQG (SEQ ID NO: 2), CDRH3 is HGRGYNGYEGAFDI (SEQ ID NO: 3), CDRL1 is RASQGISSALA (SEQ ID NO: 4), CDRL2 is DASSLES (SEQ ID NO: 5), and CDRL3 is CQQFNSYPLT (SEQ ID NO: 6).

6. The antigen-binding fragment of claim 5 comprising the antibody wherein the LCVR amino acid sequence is SEQ ID NO: 13 and the HCVR amino acid sequence is SEQ ID NO: 7.

7. The antigen-binding fragment of claim 6 comprising the antibody comprising a heavy chain and a light chain, wherein the heavy chain amino acid sequence is SEQ ID NO: 9 and the light chain amino acid sequence is SEQ ID NO: 15.

8. The antigen-binding fragment of claim 7 comprising the antibody comprising two heavy chains and two light chains, wherein each of the heavy chain amino acid sequences is SEQ ID NO: 9 and each of the light chain amino acid sequences is SEQ ID NO: 15.

* * * * *

SEQUENCE LISTING

```
<160> NUMBER OF SEQ ID NOS: 20

<210> SEQ ID NO 1
<211> LENGTH: 5
<212> TYPE: PRT
<213> ORGANISM: homo sapiens

<400> SEQUENCE: 1

Ser Tyr Trp Ile Gly
1               5

<210> SEQ ID NO 2
<211> LENGTH: 17
<212> TYPE: PRT
<213> ORGANISM: homo sapiens

<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 14
<212> TYPE: PRT
<213> ORGANISM: homo sapiens

<400> SEQUENCE: 3

His Gly Arg Gly Tyr Asn Gly Tyr Glu Gly Ala Phe Asp Ile
1               5                   10

<210> SEQ ID NO 4
<211> LENGTH: 11
<212> TYPE: PRT
<213> ORGANISM: homo sapiens

<400> SEQUENCE: 4

Arg Ala Ser Gln Gly Ile Ser Ser Ala Leu Ala
1               5                   10

<210> SEQ ID NO 5
<211> LENGTH: 7
<212> TYPE: PRT
<213> ORGANISM: homo sapiens
```

<400> SEQUENCE: 5

Asp Ala Ser Ser Leu Glu Ser
1               5

<210> SEQ ID NO 6
<211> LENGTH: 10
<212> TYPE: PRT
<213> ORGANISM: homo sapiens

<400> SEQUENCE: 6

Cys Gln Gln Phe Asn Ser Tyr Pro Leu Thr
1               5                   10

<210> SEQ ID NO 7
<211> LENGTH: 123
<212> TYPE: PRT
<213> ORGANISM: homo sapiens

<400> SEQUENCE: 7

Gln Val Gln Leu Val Gln Ser Gly Ala Ala Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Gly Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Met Val Thr Val Ser Ser
        115                 120

<210> SEQ ID NO 8
<211> LENGTH: 369
<212> TYPE: DNA
<213> ORGANISM: homo sapiens

<400> SEQUENCE: 8
caggtgcagc tggtgcagtc tggagcagcg gtgaaaaagc ccggggagtc tctgaagatc      60
tcctgtaagg gttctggata caggtttacc agctactgga tcggctgggt gcgccagatg     120
cccgggaaag cctggagtg atggggatc atctatcctg gtgactctga taccagatac       180
agcccgtcct tccaaggcca ggtcaccatc tcagccggca gtccatcag caccgcctac      240 ctgcagtgga gcagcctgaa ggcctcggac accgccatgt attactgtgc gagacatggg     300
cgtggatata atggctacga gggtgctttt gatatctggg gccaagggac aatggtcacc     360
gtctcttca                                                              369

<210> SEQ ID NO 9
<211> LENGTH: 453
<212> TYPE: PRT
<213> ORGANISM: homo sapiens

<400> SEQUENCE: 9

```
Gln Val Gln Leu Val Gln Ser Gly Ala Ala Val Lys Lys Pro Gly Glu
1               5                   10                  15
Ser Leu Lys Ile Ser Cys Lys Gly Ser Gly Tyr Arg Phe Thr Ser Tyr
            20                  25                  30
Trp Ile Gly Trp Val Arg Gln Met Pro Gly Lys Gly Leu Glu Trp Met
        35                  40                  45
Gly Ile Ile Tyr Pro Gly Asp Ser Asp Thr Arg Tyr Ser Pro Ser Phe
    50                  55                  60
Gln Gly Gln Val Thr Ile Ser Ala Gly Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Ala Arg His Gly Arg Gly Tyr Asn Gly Tyr Glu Gly Ala Phe Asp Ile
            100                 105                 110
Trp Gly Gln Gly Thr Met Val Thr Val Ser Ser Ala Ser Thr Lys Gly
        115                 120                 125
Pro Ser Val Phe Pro Leu Ala Pro Ser Ser Lys Ser Thr Ser Gly Gly
    130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Arg Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 10
<211> LENGTH: 1359
<212> TYPE: DNA
<213> ORGANISM: homo sapiens

<400> SEQUENCE: 10
caggtgcagc tggtgcagtc tggagcagcg gtgaaaaagc ccggggagtc tctgaagatc     60
tcctgtaagg gttctggata caggtttacc agctactgga tcggctgggt gcgccagatg    120
cccgggaaag gcctggagtg gatgggggatc atctatcctg gtgactctga taccagatac    180
agcccgtcct ccaaggcca ggtcaccatc tcagccggca agtccatcag caccgcctac    240
ctgcagtgga gcagcctgaa ggcctcggac accgccatgt attactgtgc gagacatggg    300
cgtggatata tggctacga gggtgctttt gatatctggg gccaagggac aatggtcacc    360
gtctcttcag ctagcaccaa gggcccatcg gtcttccccc tggcaccctc ctccaagagc    420
acctctgggg gcacagcggc cctgggctgc ctggtcaagg actacttccc cgaaccggtg    480
acggtgtcgt ggaactcagg cgccctgacc agcggcgtgc acaccttccc ggctgtccta    540
cagtcctcag gactctactc cctcagcagc gtggtgaccg tgccctccag cagcttgggc    600
acccagacct acatctgcaa cgtgaatcac aagcccagca acaccaaggt ggacaagaga    660
gttgagccca atcttgtga caaaactcac acatgcccac cgtgcccagc acctgaactc    720
ctggggggac cgtcagtctt cctcttcccc ccaaaaccca aggacaccct catgatctcc    780
cggacccctg aggtcacatg cgtggtggtg gacgtgagcc acgaagaccc tgaggtcaag    840
ttcaactggt atgtggacgg cgtggaggtg cataatgcca agacaaagcc gcgggaggag    900
cagtacaaca gcacgtaccg tgtggtcagc gtcctcaccg tcctgcacca agactggctg    960
aatggcaagg agtacaagtg caaggtctcc aacaaagccc tcccagcccc catcgagaaa   1020
accatctcca aagccaaagg gcagccccga gaaccacagg tgtacaccct gcccccatcc   1080
cgggaggaga tgaccaagaa ccaagtcagc ctgacctgcc tggtcaaagg cttctatccc   1140
agcgacatcg ccgtggagtg ggagagcaat gggcagccgg agaacaacta caagaccacg   1200
cctcccgtgc tggactccga cggctccttc ttcctctatt ccaagctcac cgtggacaag   1260
agcaggtggc agcaggggaa cgtcttctca tgctccgtga tgcatgaggc tctgcacaac   1320
cactacacgc agaagagcct ctccctgtct ccgggcaaa                           1359

<210> SEQ ID NO 11
<211> LENGTH: 472
<212> TYPE: PRT
<213> ORGANISM: homo sapiens

<400> SEQUENCE: 11

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Ala Val Lys Lys
            20                  25                  30

Pro Gly Glu Ser Leu Lys Ile Ser Cys Lys Gly Ser Gly Tyr Arg Phe
        35                  40                  45
```

```
Thr Ser Tyr Trp Ile Gly Trp Val Arg Gln Met Pro Gly Lys Gly Leu
    50                  55                  60
Glu Trp Met Gly Ile Ile Tyr Pro Gly Asp Ser Asp Thr Arg Tyr Ser
 65                  70                  75                  80
Pro Ser Phe Gln Gly Gln Val Thr Ile Ser Ala Gly Lys Ser Ile Ser
                85                  90                  95
Thr Ala Tyr Leu Gln Trp Ser Ser Leu Lys Ala Ser Asp Thr Ala Met
            100                 105                 110
Tyr Tyr Cys Ala Arg His Gly Arg Gly Tyr Asn Gly Tyr Glu Gly Ala
            115                 120                 125
Phe Asp Ile Trp Gly Gln Gly Thr Met Val Thr Val Ser Ser Ala Ser
            130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
            195                 200                 205
Ser Val Val Thr Val Pro Ser Ser Ser Leu Gly Thr Gln Thr Tyr Ile
210                 215                 220
Cys Asn Val Asn His Lys Pro Ser Asn Thr Lys Val Asp Lys Arg Val
225                 230                 235                 240
Glu Pro Lys Ser Cys Asp Lys Thr His Thr Cys Pro Pro Cys Pro Ala
            245                 250                 255
Pro Glu Leu Leu Gly Gly Pro Ser Val Phe Leu Phe Pro Pro Lys Pro
            260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
            290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
            355                 360                 365
Arg Glu Pro Gln Val Tyr Thr Leu Pro Pro Ser Arg Glu Glu Met Thr
            370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
            450                 455                 460
Ser Leu Ser Leu Ser Pro Gly Lys
465                 470
```

<210> SEQ ID NO 12
<211> LENGTH: 1419
<212> TYPE: DNA
<213> ORGANISM: homo sapiens

<400> SEQUENCE: 12

```
atgggatggt catgtatcat ccttttttctg gtagcaactg caactggagt acattcacag      60
gtgcagctgg tgcagtctgg agcagcggtg aaaaagcccg gggagtctct gaagatctcc     120
tgtaagggtt ctggatacag gtttaccagc tactggatcg gctgggtgcg ccagatgccc     180
gggaaaggcc tggagtggat ggggatcatc tatcctggtg actctgatac cagatacagc     240
ccgtccttcc aaggccaggt caccatctca gccggcaagt ccatcagcac cgcctacctg     300
cagtggagca gcctgaaggc ctcggacacc gccatgtatt actgtgcgag acatgggcgt     360
ggatataatg gctacgaggg tgcttttgat atctggggcc aagggacaat ggtcaccgtc     420
tcttcagcta gcaccaaggg cccatcggtc ttccccctgg cacctcctc caagagcacc     480
tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagagagtt     720
gagcccaaat cttgtgacaa aactcacaca tgcccaccgt gcccagcacc tgaactcctg     780
gggggaccgt cagtcttcct cttccccca aaacccaagg acaccctcat gatctcccgg     840
acccctgagg tcacatgcgt ggtggtggac gtgagccacg aagaccctga ggtcaagttc     900
aactggtatg tggacggcgt ggaggtgcat aatgccaaga caaagccgcg ggaggagcag     960
tacaacagca cgtaccgtgt ggtcagcgtc ctcaccgtcc tgcaccaaga ctggctgaat    1020
ggcaaggagt acaagtgcaa ggtctccaac aaagccctcc cagcccccat cgagaaaacc    1080
atctccaaag ccaaagggca gccccgagaa ccacaggtgt acaccctgcc cccatcccgg    1140
gaggagatga ccaagaacca gtcagcctg acctgcctgg tcaaaggctt ctatcccagc    1200
gacatcgccg tggagtggga gagcaatggg cagccggaga caactacaa gaccacgcct    1260
cccgtgctgg actccgacgg ctccttcttc ctctattcca agctcaccgt ggacaagagc    1320
aggtggcagc aggggaacgt cttctcatgc tccgtgatgc atgaggctct gcacaaccac    1380
tacacgcaga agagcctctc cctgtctccg ggcaaatga                          1419
```

<210> SEQ ID NO 13
<211> LENGTH: 107
<212> TYPE: PRT
<213> ORGANISM: homo sapiens

<400> SEQUENCE: 13

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Phe Asn Ser Tyr Pro Leu
                85                  90                  95
Thr Phe Gly Gly Gly Thr Lys Val Glu Ile Lys
            100                 105
```

<210> SEQ ID NO 14
<211> LENGTH: 273
<212> TYPE: DNA
<213> ORGANISM: homo sapiens

<400> SEQUENCE: 14

```
gccatccagt tgacccagtc tccatcctcc ctgtctgcat ctgtaggaga cagagtcacc      60
atcacttgcc gggcaagtca gggcattagc agtgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag ttt                                  273
```

<210> SEQ ID NO 15
<211> LENGTH: 214
<212> TYPE: PRT
<213> ORGANISM: homo sapiens

<400> SEQUENCE: 15

```
Ala Ile Gln Leu Thr Gln Ser Pro Ser Ser Leu Ser Ala Ser Val Gly
  1               5                  10                  15
Asp Arg Val Thr Ile Thr Cys Arg Ala Ser Gln Gly Ile Ser Ser Ala
                20                  25                  30
Leu Ala Trp Tyr Gln Gln Lys Pro Gly Lys Ala Pro Lys Leu Leu Ile
            35                  40                  45
Tyr Asp Ala Ser Ser Leu Glu Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Phe Asn Ser Tyr Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 16
<211> LENGTH: 645
<212> TYPE: DNA
<213> ORGANISM: homo sapiens

<400> SEQUENCE: 16

```
gccatccagt tgacccagtc tccatcctcc ctgtctgcat ctgtaggaga cagagtcacc    60
atcacttgcc gggcaagtca gggcattagc agtgctttag cctggtatca gcagaaacca   120
gggaaagctc ctaagctcct gatctatgat gcctccagtt tggaaagtgg ggtcccatca   180
aggttcagcg gcagtggatc tgggacagat tcactctcca ccatcagcag cctgcagcct   240
gaagattttg caacttatta ctgtcaacag tttaatagtt accctctcac tttcggcgga   300
gggaccaagg tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttag                  645
```

<210> SEQ ID NO 17
<211> LENGTH: 233
<212> TYPE: PRT
<213> ORGANISM: homo sapiens

<400> SEQUENCE: 17

```
Met Gly Trp Ser Cys Ile Ile Leu Phe Leu Val Ala Thr Ala Thr Gly
  1               5                  10                  15

Val His Ser Ala Ile Gln Leu Thr Gln Ser Pro Ser Ser Leu Ser Ala
             20                  25                  30

Ser Val Gly Asp Arg Val Thr Ile Thr Cys Arg Ala Ser Gln Gly Ile
         35                  40                  45

Ser Ser Ala Leu Ala Trp Tyr Gln Gln Lys Pro Gly Lys Ala Pro Lys
     50                  55                  60

Leu Leu Ile Tyr Asp Ala Ser Ser Leu Glu Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Gln Gln Phe Asn Ser
            100                 105                 110

Tyr Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 18
<211> LENGTH: 702
<212> TYPE: DNA
<213> ORGANISM: homo sapiens

<400> SEQUENCE: 18

```
atgggatggt catgtatcat ccttttctg gtagcaactg caactggagt acattcagcc      60
atccagttga cccagtctcc atcctccctg tctgcatctg taggagacag agtcaccatc     120
acttgccggg caagtcaggg cattagcagt gctttagcct ggtatcagca gaaaccaggg     180
aaagctccta agctcctgat ctatgatgcc tccagtttgg aaagtggggt cccatcaagg     240
ttcagcggca gtggatctgg gacagatttc actctcacca tcagcagcct gcagcctgaa     300
gattttgcaa cttattactg tcaacagttt aatagttacc ctctcacttt cggcggaggg     360
accaaggtgg agatcaaacg aactgtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702
```

<210> SEQ ID NO 19
<211> LENGTH: 520
<212> TYPE: PRT
<213> ORGANISM: homo sapiens

<400> SEQUENCE: 19

```
Met Arg Gly Ala Arg Gly Ala Trp Asp Phe Leu Cys Val Leu Leu Leu
  1               5                  10                  15

Leu Leu Arg Val Gln Thr Gly Ser Ser Gln Pro Ser Val Ser Pro Gly
             20                  25                  30

Glu Pro Ser Pro Pro Ser Ile His Pro Gly Lys Ser Asp Leu Ile Val
         35                  40                  45

Arg Val Gly Asp Glu Ile Arg Leu Leu Cys Thr Asp Pro Gly Phe Val
     50                  55                  60

Lys Trp Thr Phe Glu Ile Leu Asp Glu Thr Asn Glu Asn Lys Gln Asn
 65                  70                  75                  80

Glu Trp Ile Thr Glu Lys Ala Glu Ala Thr Asn Thr Gly Lys Tyr Thr
                 85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220
```

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
            245                 250                 255

Glu Lys Tyr Asn Ser Trp His His Gly Asp Phe Asn Tyr Glu Arg Gln
                260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
        290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
            325                 330                 335

Tyr Glu Ala Phe Pro Lys Pro Glu His Gln Gln Trp Ile Tyr Met Asn
                340                 345                 350

Arg Thr Phe Thr Asp Lys Trp Glu Asp Tyr Pro Lys Ser Glu Asn Glu
            355                 360                 365

Ser Asn Ile Arg Tyr Val Ser Glu Leu His Leu Thr Arg Leu Lys Gly
        370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
            405                 410                 415

Thr Tyr Asp Arg Leu Val Asn Gly Met Leu Gln Cys Val Ala Ala Gly
                420                 425                 430

Phe Pro Glu Pro Thr Ile Asp Trp Tyr Phe Cys Pro Gly Thr Glu Gln
            435                 440                 445

Arg Cys Ser Ala Ser Val Leu Pro Val Asp Val Gln Thr Leu Asn Ser
        450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
                500                 505                 510

Lys Glu Gln Ile His Pro His Thr
            515                 520

<210> SEQ ID NO 20
<211> LENGTH: 495
<212> TYPE: PRT
<213> ORGANISM: homo sapiens

<400> SEQUENCE: 20

Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
            20                  25                  30

Cys Thr Asp Pro Gly Phe Val Lys Trp Thr Phe Glu Ile Leu Asp Glu
        35                  40                  45

Thr Asn Glu Asn Lys Gln Asn Glu Trp Ile Thr Glu Lys Ala Glu Ala
    50                  55                  60

Thr Asn Thr Gly Lys Tyr Thr Cys Thr Asn Lys His Gly Leu Ser Asn
65                  70                  75                  80

```
Ser Ile Tyr Val Phe Val Arg Asp Pro Ala Lys Leu Phe Leu Val Asp
                85                  90                  95

Arg Ser Leu Tyr Gly Lys Glu Asp Asn Asp Thr Leu Val Arg Cys Pro
                100                 105                 110

Leu Thr Asp Pro Glu Val Thr Asn Tyr Ser Leu Lys Gly Cys Gln Gly
                115                 120                 125

Lys Pro Leu Pro Lys Asp Leu Arg Phe Ile Pro Asp Pro Lys Ala Gly
                130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
                180                 185                 190

Lys Ala Ser Tyr Leu Leu Arg Glu Gly Glu Glu Phe Thr Val Thr Cys
                195                 200                 205

Thr Ile Lys Asp Val Ser Ser Ser Val Tyr Ser Thr Trp Lys Arg Glu
                210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

Val Asn Asp Ser Gly Val Phe Met Cys Tyr Ala Asn Asn Thr Phe Gly
                260                 265                 270

Ser Ala Asn Val Thr Thr Thr Leu Glu Val Val Asp Lys Gly Phe Ile
                275                 280                 285

Asn Ile Phe Pro Met Ile Asn Thr Thr Val Phe Val Asn Asp Gly Glu
290                 295                 300

Asn Val Asp Leu Ile Val Glu Tyr Glu Ala Phe Pro Lys Pro Glu His
305                 310                 315                 320

Gln Gln Trp Ile Tyr Met Asn Arg Thr Phe Thr Asp Lys Trp Glu Asp
                325                 330                 335

Tyr Pro Lys Ser Glu Asn Glu Ser Asn Ile Arg Tyr Val Ser Glu Leu
                340                 345                 350

His Leu Thr Arg Leu Lys Gly Thr Glu Gly Gly Thr Tyr Thr Phe Leu
                355                 360                 365

Val Ser Asn Ser Asp Val Asn Ala Ala Ile Ala Phe Asn Val Tyr Val
                370                 375                 380

Asn Thr Lys Pro Glu Ile Leu Thr Tyr Asp Arg Leu Val Asn Gly Met
385                 390                 395                 400

Leu Gln Cys Val Ala Ala Gly Phe Pro Glu Pro Thr Ile Asp Trp Tyr
                405                 410                 415

Phe Cys Pro Gly Thr Glu Gln Arg Cys Ser Ala Ser Val Leu Pro Val
                420                 425                 430

Asp Val Gln Thr Leu Asn Ser Ser Gly Pro Pro Phe Gly Lys Leu Val
                435                 440                 445

Val Gln Ser Ser Ile Asp Ser Ser Ala Phe Lys His Asn Gly Thr Val
                450                 455                 460

Glu Cys Lys Ala Tyr Asn Asp Val Gly Lys Thr Ser Ala Tyr Phe Asn
465                 470                 475                 480

Phe Ala Phe Lys Gly Asn Asn Lys Glu Gln Ile His Pro His Thr
                485                 490                 495
```